(12) United States Patent
Hesse et al.

(10) Patent No.: US 6,686,506 B1
(45) Date of Patent: Feb. 3, 2004

(54) PROCESS FOR THE PREPARATION OF ORGANIC DISULFIDES

(75) Inventors: Werner Hesse, Obrigheim (DE); Hans-Josef Sterzel, Dannstadt-Schauernheim (DE); Christian Tragut, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/831,914

(22) PCT Filed: Nov. 25, 1999

(86) PCT No.: PCT/EP99/09145
§ 371 (c)(1), (2), (4) Date: May 25, 2001

(87) PCT Pub. No.: WO00/31029
PCT Pub. Date: Jun. 2, 2000

(30) Foreign Application Priority Data

Nov. 25, 1998 (DE) .......................... 198 54 427

(51) Int. Cl.⁷ ............................................. C07C 319/00
(52) U.S. Cl. ............................. 568/26; 568/21; 568/25
(58) Field of Search ............................ 568/21, 25, 26

(56) References Cited

U.S. PATENT DOCUMENTS

| | | | | |
|---|---|---|---|---|
| 2,820,062 A | | 1/1958 | Folkins et al. | |
| 3,277,180 A | * | 10/1966 | Bapseres et al. | |
| 3,308,166 A | * | 3/1967 | Biensan et al. | |
| 3,314,999 A | * | 4/1967 | Bapseres et al. | |
| 5,026,915 A | * | 6/1991 | Buchholz et al. | 568/26 |
| 5,202,494 A | | 4/1993 | Roberts et al. | |
| 5,659,086 A | * | 8/1997 | Pauwels et al. | 568/26 |
| 5,786,511 A | * | 7/1998 | Arretz et al. | 568/21 |
| 6,020,529 A | * | 2/2000 | Fremy et al. | 568/21 |

FOREIGN PATENT DOCUMENTS

| | | |
|---|---|---|
| EP | 0 171 092 | 2/1986 |
| EP | 0 202 420 | 11/1986 |
| FR | 1358398 | 3/1964 |
| GB | 987358 | 3/1965 |
| WO | WO 98/34914 | 8/1998 |

* cited by examiner

Primary Examiner—Jean F. Vollano
(74) Attorney, Agent, or Firm—Oblon, Spivak, McClelland, Maier & Neustadt, P.C.

(57) ABSTRACT

The invention relates to a process for the preparation of organic disulfides by oxidation of mercaptans with sulfur dissolved in an organic disulfide using an amine as catalyst, where the mercaptans are used as "crude mercaptan stream" from a reaction of alcohols with hydrogen sulfide over a catalyst suitable for mercaptan synthesis. Furthermore, the invention relates to the use of the organic disulfides for the preparation of alkanesulfonic acids.

31 Claims, 1 Drawing Sheet

PROCESS FOR THE PREPARATION OF ORGANIC DISULFIDES

BACKGROUND OF THE INVENTION

1. Field of the Invention

The application is a 371 of PCT/EP99/09145 filed Nov. 25, 1999, now WO 00/31029.

The present invention relates to a process for the preparation of organic disulfides.

Various processes for the preparation of organic disulfides are known from the prior art.

2. Description of the Background

EP-A 0 171 092 describes a process for the preparation of dialkyl disulfides in which alcohol, sulfur and hydrogen sulfide are reacted directly to give dialkyl disulfides and water. The process is preferably carried out over a zeolite-based catalyst, at temperatures of from 200 to 400° C. and in a pressure range from atmospheric pressure to 600 psig. A disadvantage of this process is that multicomponent product mixtures are obtained from which the dialkyl disulfide can only be isolated in poor yields (approximately 50% of the theoretical yield).

U.S. Pat. No. 5,202,494 describes a process in which mercaptan is reacted with oxygen over an $MgO/Na_2O$-doped aluminum oxide catalyst to give dialkyl disulfide and water. The process produces high-boiling components, which have to be removed from the system during distillative work-up.

FR-B 1 358 398 discloses a process for the preparation of dialkyl disulfides from mercaptans and elemental sulfur in which the sulfur is used in the form of a solution in an organic solvent, in particular in an organic dialkyl disulfide. The catalysts used are amines. A disadvantage of this process is that clean, and therefore expensive, mercaptans have to be used as starting materials.

SUMMARY OF THE INVENTION

It is therefore an object of the present invention to provide a process for the preparation of organic disulfides which starts from low cost and readily available raw materials and provides the desired dialkyl disulfide in good yields.

We have found that this object is achieved by a process for the preparation of organic disulfides by oxidation of mercaptans with sulfur dissolved in an organic disulfide using an amine as catalyst. The process according to the invention comprises using the mercaptans as "crude mercaptan stream" from a reaction of alcohols with hydrogen sulfide over a catalyst suitable for mercaptan synthesis.

BRIEF DESCRIPTION OF THE DRAWING

The drawing illustrates a flow diagram for the two-stage synthesis of dimethyl disulfide (DMDS).

DETAILED DESCRIPTION OF THE PREFERRED EMBODIMENT

Figure 1:
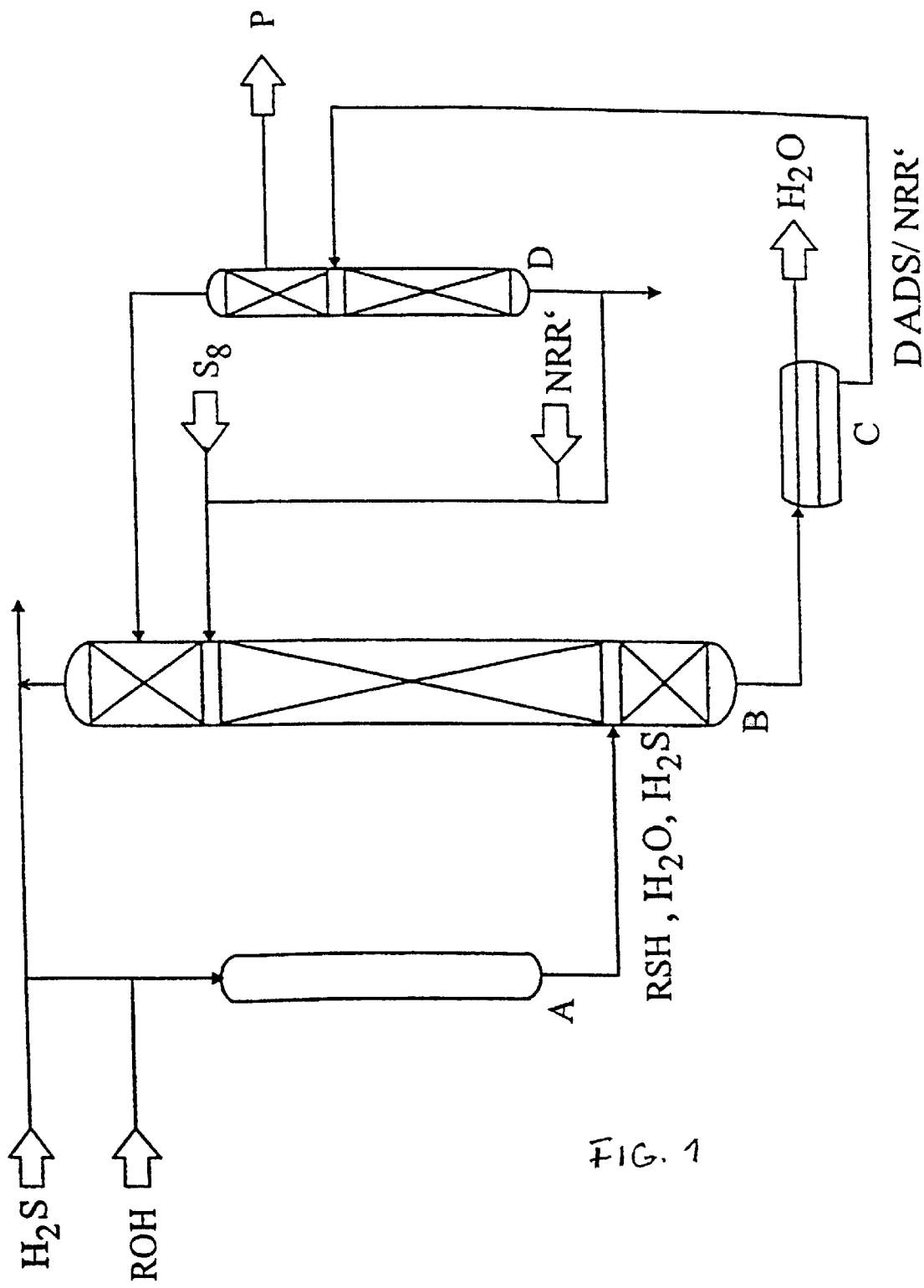

For the purposes of the present invention, a "crude mercaptan stream" is a mercaptan stream not purified by extraction or distillation from the synthesis of mercaptans from alcohols and hydrogen sulfide. The "crude mercaptan stream" can also comprise hydrogen sulfide which has not fully reacted, water and, as secondary components, dialkyl sulfide, small amounts of alcohol and dialkyl ether.

Such a "crude mercaptan stream" is usually purified by complex, multistage pressure distillation, which involves high costs. By dispensing with the distillation stage, a pressure stage is avoided, and the entire process can be carried out without pressure. This results in a cost advantage since complex pressurized apparatus is not required. Increased safety is also ensured.

The "crude mercaptan" used is prepared by reaction of alcohol and hydrogen sulfide over a catalyst suitable for mercaptan synthesis. The reaction is preferably carried out at temperatures between 350 and 450° C. in the gaseous phase. The catalysts which can be used are all those catalysts known to the person skilled in the art and suitable for mercaptan synthesis. Preference is given to doped aluminum oxides, the dopants used being 1. KOH (EP-A 0 564 706), 2. $K_2CO_3$ (EP-A 0 749 961), 3. $B_2O_3$, $K_3WO_4$ (React. Kinet. Catal. Lett. 36, 1, p. 159), 4. CaO (EP-A 0 564 706). Particular preference is given to using potassium tungstate on activated $Al_2O_3$ as catalyst, as are described in U.S. Pat. No. 3,935,276 and Hillis O. Folkins and Elmer L. Miller, I&EC Process Design and Development, Vol. 1, No. 4, October 1962. To reduce the risk of emissions the process according to the invention is usually carried out at from 1 to 3 bar absolute, preferably approximately atmospheric, instead of the otherwise customary 10 to 15 bar.

To produce the "crude mercaptan stream" gaseous hydrogen sulfide and alcohols are preferably charged to a simple tubular reactor and reacted over a solid catalyst, preferably potassium tungstate on activated $Al_2O_3$. This stream of gas is oxidized with sulfur dissolved in an organic disulfide using an amine as catalyst to give organic disulfides.

The organic disulfide used as solvent and the organic disulfide to be prepared are preferably the same compound. This means that it is not necessary to separate off an additional solvent.

The following concepts relate to the reaction:

When sulfur dissolves in organic disulfides organic polysulfides are formed. According to the invention, organic polysulfides are sulfides of the formula $R(-S)_n-R$, in which the radicals R are independent of the organic disulfide used or the mercaptan used—if mercaptan is present in the actual reaction—i.e. R does not have to be of the same type, although this is preferable in order to avoid additional processing steps (end product and solvent preferably the same). n is generally an integer from 3 to 12, preferably from 3 to 9. Concentrated solutions additionally comprise also physically dissolved $S_8$ sulfur. The dissolved sulfur and the organic polysulfides jointly symbolized below by "S") react at temperatures between room temperature and the boiling point of the organic disulfide to be prepared in the presence of mercaptans in accordance with the following equation to give organic disulfides.

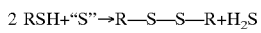

Here, the dissolved sulfur and the higher polysulfides react most quickly, while lower polysulfides as far as the trisulfide (n=3) only react slowly. Because of the hydrogen sulfide still present in the "crude mercaptan stream" an equilibrium according to the following equation between organic disulfides and organic trisulfides is, for example, assumed:

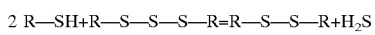

Accordingly, organic trisulfide formed does not react completely to give organic disulfide. Thus, the end product obtained is not a pure polysulfide-free organic disulfide, but always a mixture of organic disulfides and organic trisulfides, which is further purified. Furthermore, the product mixture further comprises the amine used as catalyst.

Amines which can be used in the process according to the invention are primary, secondary and tertiary aliphatic or aromatic amines. Preference is given to using primary, secondary or tertiary aliphatic amines. Particular preference is given to liquid or solid amines having a boiling point above the boiling point of the organic disulfides used and an extremely low water solubility of generally less than 0.5 g/l. Very particularly preferably, the amines used have a boiling point above 140° C. and a water solubility of less than 0.1 g/l. In particular, very particularly preferred amines are primary, secondary or tertiary amines having from 6 to 60 carbon atoms. For example, tridecylamine, fatty amines such as N,N-dimethyl-$C_{12}/C_{14}$-amine, dicyclohexylamine are suitable. The amine is generally used in an amount of from 0.1 to 10% by weight, preferably from 0.5 to 5% by weight, particularly preferably from 1 to 3% by weight, based on the sulfur used.

The process according to the invention is suitable for the preparation of organic disulfides from any mercaptans. In general, mercaptans containing aliphatic, cycloaliphatic, aryl, arylalkyl or aralkyl radicals are used. The aliphatic radicals can be linear or branched, unsubstituted or substituted by functional groups such as hydroxyl, halogen, thio, thioether, sulfonyl, sulfoxyl, sulfenyl, amino, imino, nitro or nitroso groups, saturated or mono- or polyunsaturated. The cycloaliphatic radicals can contain double bonds and/or hetero atoms, in particular S or N. For example, it is possible to use methyl, ethyl, n-propyl, isopropyl, n-butyl, isobutyl, amyl, hexyl or benzyl mercaptan. This gives dimethyl, diethyl, di-n-propyl, diisopropyl, di-n-butyl, diisobutyl, diamyl, dihexyl or dibenzyl disulfides. Preference is given to using mercaptans containing saturated aliphatic radicals having from 1 to 3 carbon atoms such as methyl, ethyl or n-propyl mercaptan. Particular preference is given to methyl mercaptan. The particularly preferred prepared organic disulfide is accordingly dimethyl disulfide.

The process according to the invention is preferably carried out as a continuous process. The process is particularly preferably a closed loop, i.e. byproduced products of value can be reused.

The present invention thus further relates to a process comprising the following steps:
(a) reaction of alkanols with hydrogen sulfide over a suitable catalyst to give a "crude mercaptan stream", comprising mercaptan, water, hydrogen sulfide and small amounts of other by-products such as organic sulfide and ether,
(b) reaction of the "crude mercaptan stream" with sulfur dissolved in an organic disulfide with catalysis with an amine in a reaction column, where low-boiling components which form are returned to step (a),
(c) phase separation of the resulting mixture comprising aqueous phase, which is removed from the system, and organosulfur phase,
(d) purification of the organosulfur phase, which optionally comprises lowboiling components, the desired organic disulfide, polysulfides, dissolved sulfur, amine and small amounts of other by-products, where the organic disulfide is taken off, any low-boiling components which form are returned to step (a), and polysulfides (n=3 to 12) which form, dissolved sulfur and amine are returned to step (b), with addition of sulfur and optionally fresh amine,
where the phase separation and the removal from the system of the aqueous phase in step (c) can take place immediately following step (a) or immediately following step (b).

The preparation of the "crude mercaptan stream" is preferably carried out in a simple tubular reactor in the gaseous phase, and the resulting stream of gas is then introduced into the lower section of a reaction column, for example a bubble-cap column. In step (b) this stream of gas meets countercurrently with a solution of sulfur in organic disulfide in which the amine required as catalyst has been dissolved. Low-boiling components produced at the top of the reaction column can be returned to step (a). At the bottom of the reaction column, organic disulfide in a mixture with organic trisulfide and optionally other lower polysulfides is obtained. Furthermore, the bottom of the reaction column also comprises the amine, and water introduced from the mercaptan synthesis.

The still temperature in the reaction column is generally from 20 to 120° C., preferably from 50 to 100° C., particularly preferably from 90 to 95° C. The head temperature is generally from −20 to +30° C., preferably from 0 to +20° C., particularly preferably from 0 to +10° C. Step (b) is generally carried out at atmospheric pressure.

The aqueous phase is separated from the organosulfur phase in step (c), preferably in a phase separator, and disposed of. This phase separation can also be carried out directly after the mercaptan synthesis (step (a)). If the aqueous phase is separated off immediately after step (b), the bottom temperature in the reaction column should preferably be greater than 80° C., preferably between 90 and 95° C., so that the aqueous phase to be discharged contains only small amounts of low-boiling sulfur compounds such as hydrogen sulfide. On the other hand, the temperature should not be so high that the water covers large sections of the column and can no longer be discharged via the still.

An advantage of this process according to the invention is that hydrogen sulfide present in the reaction mixture can be recycled from the top of the reaction column to the mercaptan synthesis. Secondary components such as organic sulfide, alcohol and ether are also recycled in this manner and reacted in the tubular reactor to give mercaptan (step (a)).

Following removal of the water, the organosulfur phase is purified (step (d)). The purification can be carried out by any suitable method. Preference is given to purification by distillation, particular preference to distillation at reduced pressure. Using reduced pressure it is possible to avoid excessively high still temperatures, thus preventing decomposition of organic polysulfides and sulfur to, for example, $CS_2$ and mercaptan.

The distillation is carried out in a distillation column which preferably contains at least ten theoretical plates. Small amounts of low-boiling components obtained during the distillation, such as mercaptan, organic sulfide or $CS_2$, are separated off and can be returned to step (a). The organic disulfide is drawn off, the drawing-off preferably being carried out in a sidestream takeoff of the distillation column. The still solution or some of the still solution is returned to step (b) by dissolving elemental sulfur, preferably in liquid form, in this mixture and, where appropriate, replenishing the catalyst amine, and reintroducing this mixture into the upper section of the reaction column.

The process according to the invention provides a closed system in which, according to the net equation:

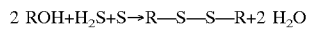

organic disulfides can be prepared continuously using a prereactor and two columns. The organic disulfides prepared in the process according to the invention can be used in particular for the preparation of sulfonic acids. In this connection, they are suitable in particular for the preparation of alkylsulfonic acids, preferably by oxidation of the organic disulfides with $HNO_3$.

In the accompanying drawing, FIG. 1 shows an exemplary process diagram for the synthesis of the organic disulfides.

Here,

A is a tubular reactor in which step (a) is carried out;
B is a reaction column in which step (b) is carried out;
C is a phase separator in which step (c) is carried out;
D is a distillation column in which step (d) is carried out;
NRR' is amine used as catalyst in step (b);
P is purified product (organic disulfide);
DADS is organic disulfide.

The other abbreviations are given in the text above.
The examples below further illustrate the invention.

EXAMPLES

1. Example in a Continuous Experimental Plant

The two-stage dimethyl disulfide (DMDS) synthesis was carried out in a continuously operating laboratory apparatus which comprises all components of the flow diagram (FIG. 1).

The MeSH tubular reactor (600 mm long, 25 mm in diameter) was filled with a self-prepared catalyst of aluminum oxide with 14% by weight of potassium tungstate. At a temperature of 400° C. (middle of the reactor) and a pressure of 1.1 $bar_{abs}$ 48 g/h (1.5 mol) of gaseous methanol, 34 g/h (1 mol) of hydrogen sulfide and 40 g/h of back gas from the reaction column (composition: 72% of $H_2S$, 12% of MeSH, 16% of dimethyl sulfide (DMS), small amounts of methanol and dimethyl ether) were fed into the tubular reactor. The gas composition at the reactor outlet was: 13.0% of $H_2S$, 50.8% of MeSH, 10.3% of DMS, 21.6% of $H_2O$, 2.4% of MeOH, 1.2% of dimethyl ether (DME).

This gas enters the lower section of the reaction column (bubble-cap column containing 20 plates) and flows countercurrently to the downwardly flowing sulfur solution (still solution from distillation column, to which 19 g/h of sulfur and 0.1 g/h of dicyclohexylamine is metered in), where MeSH reacts with formation of $H_2S$. The gas exiting at the top of the column and having the composition above is compressed, as back gas, and returned to the MeSH tubular reactor, where a relatively small proportion of the gas is removed from the system. The still solution heated to about 90° C. is two-phase, the upper phase being the water formed in the MeSH synthesis. The phases are passed to a phase separator, where they are separated and the upper, aqueous phase is collected in a discharge container (26 g/h). The lower organosulfur phase is passed at the side to a distillation column which is operated at subatmospheric pressure (300 mbar). The product DMDS was isolated in a sidestream takeoff (53 g/h) and had a purity of 99.6% (0.1% of dimethyl trisulfide, 0.3% of low-boiling components such as dimethyl sulfide (DMS), MeSH, $CS_2$). The yield of DMDS, based on the sulfur used, is thus 94.9%. The low-boiling components produced at the top of the distillation column were in this case not recycled to the top of the reaction column as in FIG. 1.

2. Comparative Example

A solution of 50 g of sulfur, 25 g of DMDS, 1 g of triisobutylamine was introduced into a thermostated glass tube fitted with frit and thermostated at 60° C. Gaseous methyl mercaptan was then passed upwardly through the solution via the frit from a steel cylinder in an amount of 24 g/h. The compositions of gas and liquid phases were analyzed by gas chromatography as a function of time. At the start of the reaction a large part of the methyl mercaptan was reacted to form hydrogen sulfide. The gas phase over the liquid initially comprised about 75% of $H_2S$. The content of $H_2S$ then dropped until, at the end of the reaction, almost pure methyl mercaptan passed through the solution. The reaction had ended after 13 h. 118 g of solution were obtained which had the following composition: 0.5% of $H_2S$, 5.8% of MeSH, 55.2% of DMDS, 32.9% of dimethyl trisulfide, 4.2% of dimethyl polysulfides, 0.9% of amine.

3. Comparative Example

A solution of 50 g of sulfur, 25 g of DMDS, 1 g of tridecylamine was introduced into a thermostated glass tube fitted with frit and thermostated at 60° C. Gaseous methyl mercaptan was then passed upwardly through the solution via the frit from a steel cylinder in an amount of 24 g/h. The compositions of gas and liquid phases were analyzed by gas chromatography as a function of time. At the start of the reaction a large part of the methyl mercaptan was reacted to form hydrogen sulfide. The gas phase over the liquid initially comprised about 79% of $H_2S$. The content of $H_2S$ then dropped until, at the end of the reaction, almost pure methyl mercaptan passed through the solution. The reaction had ended after 12 h. 156 g of solution were obtained which had the following composition: 0.1% of $H_2S$, 7.7% of MeSH, 90.5% of DMDS, 0.8% of dimethyl trisulfide, no dimethyl polysulfides, 0.8% of amine. The yield of DMDS, based on the sulfur used, is 83%. The losses arise as a result of the gaseous discharge of DMDS with the reaction gases.

We claim:

1. A continuous process for the preparation of an organic disulfide comprising:
   oxidizing a mercaptan with sulfur dissolved in an organic disulfide in the presence of an amine catalyst,
   wherein said mercaptan is present in a crude mercaptan stream, which is obtained from a reaction of an alcohol with hydrogen sulfide in the presence of a catalyst suitable for mercaptan synthesis, and
   wherein said amine is a primary, secondary, or tertiary amine having from 6 to 60 carbon atoms, and which has a boiling point above the boiling point of said organic disulfide, and a water solubility of less than 0.5 g/l.

2. The process of claim 1, further comprising producing the crude mercaptan stream by reacting an alcohol with hydrogen sulfide in the presence of a catalyst suitable for mercaptan synthesis.

3. The process of claim 2, wherein the catalyst suitable for mercaptan synthesis comprises potassium tungstate on activated $Al_2O_3$.

4. The process of claim 1, wherein the amine is a primary amine.

5. The process of claim 1, wherein the amine is a secondary amine.

6. The process of claim 1, wherein the amine is a tertiary amine.

7. The process of claim 1, wherein the amine is liquid.

8. The process of claim 1, wherein the amine is solid.

9. The process of claim 1, wherein said amine has a boiling point above 140° C.

10. The process of claim 1, wherein said amine has a water solubility of less than 0.1 g/l.

11. The process of claim 1, wherein said amine has a boiling point above 140° C. and a water solubility of less than 0.1 g/l.

12. The process of claim 1, wherein said amine has 12 to 60 carbons.

13. The process of claim 1, wherein said amine has 30 to 60 carbons.

14. The process of claim 1, wherein said amine is dicyclohexylamine.

15. The process of claim 1, wherein said amine is N,N-dimethyl-$C_{12}$/$C_{14}$ amine (a mixture of N,N-dimethyl-$C_{12}$ amine and N,N-dimethyl-$C_{14}$ amine).

16. The process of claim 1, wherein said amine is tridecylamine.

17. The process of claim 1, wherein said amine is trisobutylamine.

18. The process of claim 1, wherein the amine is used in an amount ranging from 0.1 to 10% by weight based on the sulfur used.

19. The process of claim 1, wherein the amine is used in an amount ranging from 0.5 to 5% by weight based on the sulfur used.

20. The process of claim 1, wherein said mercaptan is an aliphatic mercaptan.

21. The process of claim 1, wherein said mercaptan is a cycloaliphatic mercaptan.

22. The process of claim 1, wherein said mercaptan is an aryl mercaptan.

23. The process of claim 1, wherein said mercaptan is an arylalkyl or alkylaryl mercaptan.

24. The process of claim 1, wherein said mercaptan is methyl mercaptan.

25. The process of claim 1, wherein said mercaptan is ethyl mercaptan.

26. The process of claim 1, wherein said mercaptan is n-propyl mercaptan.

27. The process of claim 1, wherein the organic disulfide to be prepared and the organic disulfide in which the sulfur is dissolved are the same compound.

28. The process of claim 1, which is a closed loop process.

29. A process comprising:
   (a) reacting an alkanol with hydrogen sulfide over a catalyst to form a crude mercaptan stream comprising mercaptan, water, and hydrogen sulfide;
   (b) reacting the crude mercaptan stream with sulfur dissolved in an organic disulfide in the presence of an amine catalyst in a reaction column, and returning any low-boiling components which form to (a), wherein said amine catalyst is a primary, secondary, or tertiary amine having from 6 to 60 carbon atoms, a boiling point above the boiling point of said organic disulfide, and a water solubility of less than 0.5 g/l;
   (c) phase separating the resulting mixture comprising aqueous phase, which is removed from the system, and organosulfur phase;
   (d) purifying the organosulfur phase, which optionally comprises low-boiling components, the desired organic disulfide, polysulfides, amine and other by-products, wherein the organic disulfide is removed, any low-boiling components which form are returned to (a), and polysulfides which form and amine are returned to (b), with addition of sulfur and optionally amine;
   wherein the phase separation and the removal from the system of the aqueous phase in (c) takes place immediately following (a) or (b).

30. The process of claim 29, wherein the purification in (d) is carried out by distillation at reduced pressure.

31. A continuous process for the preparation of an organic disulfide comprising:
   (a) reacting an alkanol with hydrogen sulfide over a catalyst to form a crude mercaptan stream comprising mercaptan, water, and hydrogen sulfide;
   (b) reacting the crude mercaptan stream with sulfur dissolved in an organic disulfide in the presence of an amine catalyst, which is a liquid or solid and has a boiling point above the boiling point of the organic disulfide and a water solubility of less than 0.5%, in a reaction column, where low-boiling components which form are returned to (a);
   (c) phase separating the resulting mixture comprising an aqueous phase, which is removed from the system, and an organosulfur phase;
   (d) purifying the organosulfur phase, which optionally comprises low-boiling components, the desired organic disulfide, polysulfides, amine and other by-products by distillation under reduced pressure, wherein the organic disulfide is removed, any low-boiling components which form are returned to (a), and polysulfides which form and amine are returned to (b), with addition of sulfur and optionally amine;
   wherein the phase separation and the removal from the system of the aqueous phase in (c) takes place immediately following (a) or (b).

* * * * *